United States Patent
Huth et al.

(10) Patent No.: US 8,691,287 B2
(45) Date of Patent: Apr. 8, 2014

(54) OPHTHALMIC SYSTEM WITH SYNERGISTIC PROPERTIES

(75) Inventors: Stanley W. Huth, Newport Beach, CA (US); Simon Kilvington, Tustin, CA (US); Simon Cheung, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 120 days.

(21) Appl. No.: 13/240,916

(22) Filed: Sep. 22, 2011

(65) Prior Publication Data

US 2012/0288470 A1 Nov. 15, 2012

Related U.S. Application Data

(63) Continuation-in-part of application No. 13/103,759, filed on May 9, 2011, now abandoned.

(51) Int. Cl.
| | |
|---|---|
| *A01N 59/16* | (2006.01) |
| *A01N 25/00* | (2006.01) |
| *A01N 25/30* | (2006.01) |
| *A01N 25/32* | (2006.01) |
| *A01N 33/04* | (2006.01) |
| *A01N 33/12* | (2006.01) |

(52) U.S. Cl.
USPC ............ 424/618; 206/5.1; 424/405; 424/406; 424/412; 424/DIG. 6; 514/635; 514/642; 514/769; 514/784; 514/974; 514/975

(58) Field of Classification Search
None
See application file for complete search history.

(56) References Cited

U.S. PATENT DOCUMENTS

| | | | |
|---|---|---|---|
| 5,320,843 A | 6/1994 | Raheja et al. | |
| 6,930,077 B2 * | 8/2005 | Glick et al. | 510/112 |
| 6,936,640 B2 | 8/2005 | McQueen et al. | |
| 7,666,823 B2 * | 2/2010 | Minick | 510/112 |

FOREIGN PATENT DOCUMENTS

| | | | |
|---|---|---|---|
| WO | WO9534327 A1 | 12/1995 | |
| WO | WO 0038552 A1 * | 7/2000 | |
| WO | WO2008109598 A2 | 9/2008 | |

OTHER PUBLICATIONS

International Search Report and Written Opinion for Application No. PCT/US2012/037098, mailed on Sep. 28, 2012, 10 pages.
Alonso A., et al., "*Stenotrophomonas maltophilia* D457R Contains a Cluster of Genes from Gram-Positive Bacteria Involved in Antibiotic and Heavy Metal Resistance," Antimicrobial Agents and Chemotherapy, 2000, vol. 44 (7), pp. 1778-1782.
Amos C.F., et al., "Clinical and Laboratory Testing of a Silver-Impregnated Lens Case," Contact Lens & Anterior Eye, 2006, vol. 29 (5), pp. 247-255.
Dantam J., et al., Biocidal Efficacy of Silver Impregnated Contact Lens Storage Cases In Vitro, 17 pages, (2011).
Holmes A., et al., "Comparison of Two Multimetal Resistant Bacterial Strains: *Enterobacter* sp. YSU and *Stenotrophomonas maltophilia* ORO2," Current Microbiology, 2009, vol. 59 (5), pp. 526-531.
Huang H.I., et al., "In Vitro Efficacy of Copper and Silver Ions in Eradicating *Pseudomonas Aeruginosa, Stenotrophomonas maltophilia* and *Acinetobacter baumannii*: Implications for On-Site Disinfection for Hospital Infection Control," Water Research, 2008, vol. 42 (1-2), pp. 73-80.
Pages D., et al., "Heavy Metal Tolerance in *Stenotrophomonas maltophilia*," PLoS One, 2008, vol. 3 (2), pp. e1539.
Powell C.H., et al., "Lipophilic Versus Hydrodynamic Modes of Uptake and Release by Contact Lenses of Active Entities used in Multipurpose Solutions," Contact Lens & Anterior Eye, 2010, vol. 33 (1), pp. 9-18.
Willcox M.D., et al., "Contact Lens Case Contamination During Daily Wear of Silicon Hydrogels," Optometry & Vision Science, 2010, vol. 87 (7), pp. 456-464.

* cited by examiner

*Primary Examiner* — Abigail Fisher
*Assistant Examiner* — Frank Choi
(74) *Attorney, Agent, or Firm* — Abbott Medical Optics Inc.

(57) ABSTRACT

Disclosed herein are ophthalmic cleaning systems and methods for their use, which comprise an ophthalmic solution and lens case, wherein the solution includes dual disinfectants and the lens case includes silver. When the lens case is combined with the solution according to the system of the present invention, it surprisingly exhibits synergistic activity which results in a faster antimicrobial activity.

2 Claims, No Drawings

OPHTHALMIC SYSTEM WITH SYNERGISTIC PROPERTIES

This application is a continuation-in-part application of U.S. patent application Ser. No. 13/103,759, entitled "Ophthalmic System With Synergistic Properties", filed May 9, 2011.

FIELD OF THE INVENTION

Disclosed herein are compositions and methods for contact lens care. More particularly, the invention relates to the synergistic use of certain ophthalmic compositions with antimicrobial lens cases to disinfect contact lenses.

BACKGROUND OF THE INVENTION

Most contact lenses that will directly contact the eye require a composition, for example, to store, condition, rinse, or reduce the microbial load on the lens. Most, if not all, of the compositions used for contact lens treatment require an additive with antimicrobial, disinfection, and/or preservative capabilities. The antimicrobial/preservative should be designed to cause minimal ocular irritation or user discomfort since this antimicrobial/preservative will likely come into contact with the eye (either directly via solution carry-over when the contact lens is placed into the eye or via a lens through chemical uptake and subsequent release into the eye.)

Many different microorganisms may be found on contact lenses or in lens cases. *Stenotrophomonas maltophilia* is a gram-negative bacterium which is the second most common gram-negative general clinical isolate after *Pseudomonas aeruginosa*. *S. maltophilia* is emerging as an important ocular pathogen: 1/1339 ocular specimens were *S. maltophilia* in the 1970s, 1/413 in the 1980s, and 1/363 in the 1990s through 1995. *Stenotrophomonas* is not an uncommon cause of microbial keratitis, infiltrative keratitis, and contact lens acute red eye among lens wearers. *S. maltophilia* enhances biofilm formation by *P. aeruginosa* and likely *P. fluorescens* and in so doing may facilitate other infections. *S. maltophilia* has high binding to and internalization into *Acanthamoeba* and has been reported to have the second highest growth enhancement of *Acanthamoeba*. It is known to be an important food source for *Acanthamoeba* species and thought to contribute to *Acanthamoeba* keratitis among contact lens wearers for this reason. In this context, *S. maltophilia* has been isolated as a co-contaminant of contact lenses and solutions, along with *Acanthamoeba*. In 2006, combined *Acanthamoeba* and *S. maltophilia* keratitis was reported. *Delftia acidovorans* is another gram-negative bacterium which is also an ocular pathogen, although reported to occur less frequently in ocular infections than *Stenotrophomonas*. *D. acidovorans* has also been reported as a food source for *Acanthamoeba*. *S. maltophilia* and *D. acidovorans* are among the top 3 most frequently isolated gram-negative bacteria in contact lens cases. Contact lens storage case contamination is associated with contact lens contamination, which leads to ocular infection. Importantly, it can be difficult for some contact lens cleaning solutions to satisfactorily disinfect against *S. maltophilia* and *D. acidovorans* and thus prevent infections arising from these organisms.

Many multi-purpose solutions (MPSs) that may be used to clean, disinfect, and wet contact lenses, followed by direct insertion into the eye, are available. Multi-purpose solutions must be strong enough to kill harmful microorganisms that may be present or grow on the lenses while being gentle enough to contact the eyes. Such a solution also must be compatible with the many contact lens materials, including the silicone hydrogel materials. Measures of contact lens compatibility include contact lens discoloration, physical parameter change, fragility, and uptake/release of solution components, especially antimicrobial agents. Contact lens care solutions, such as MPSs, attempt to balance cleaning and disinfection ability with safety and comfort on the eyes. The addition of more effective disinfecting agents usually has the effect of reducing contact lens material compatibility or ocular comfort of the solution. One way to achieve additional material compatibility and comfort is to reduce the amount of disinfecting agent. However, conventional knowledge dictates that this results in lower antimicrobial efficacy. While many antimicrobials have been developed for ophthalmic use, many of these compounds can be absorbed into lenses themselves, thus decreasing their efficacy. One way to address the absorption issue is to increase the concentration of the antimicrobial. However, this may cause irritation in the eye (particularly when the antimicrobial easily absorbs into the lens). Thus, there is a continual challenge to identify novel ways to improve disinfection without sacrificing user comfort.

One way for a contact lens wearer to increase the biocidal activity of their ophthalmic solution is to use that solution in combination with a silver-coated or silver-impregnated lens case (see, for example, U.S. Pat. No. 5,320,843, to Raheja, et al.). However, such a combination does not always provide increased activity against all organisms, and can even be unreliable against individual organisms (see for example, Dantam et al., Biocidal Efficacy of Silver Impregnated Contact Lens Storage Cases In Vitro, IVOS, 2010.) This article discusses the varying efficacy of three different lens cases against different microorganisms and notes that the lens cases, which the author noted as using broadly similar silver impregnation technology, provide inconsistent biocidal activity against various microorganisms, and minimal if any biocidal activity against specific microorganisms.

There is need for a contact lens cleaning system and method which consistently provides increased biocidal efficacy without causing increased ocular irritation or user discomfort. The disclosed systems and methods address this need by providing synergistic activity against microorganisms which are known to impact contact lens wearers.

DEFINITION OF TERMS

Antimicrobial: As used herein, the term "antimicrobial" refers to any agent or action that results in biocidal, antimicrobial, antibacterial, or antifungal activity against any microbe. A skilled artisan will appreciate that antimicrobial as used herein also refers to a disinfectant or preservative (e.g., of an ocular solution).

Ophthalmic: As used herein, the term "ophthalmic" or ophthalmic composition/solution refers to anything associated with the eyes, including compositions to treat ocular conditions (e.g., dry eye or infection) and contact lens compositions (e.g., re-wetters, disinfecting solutions, storage solutions, rinsing solutions, and multi-purpose solutions). Of course, multi-purpose contact lens care solutions are those that may be used to re-wet, disinfect, clean, store and rinse contact lenses. The antimicrobial component disclosed herein allows a user to remove a contact lens exposed to the component and place the lens directly in the user's eye for safe and comfortable wear; or, after the lens is exposed to the antimicrobial component (or a composition containing it), it may be rinsed with another quantity of the antimicrobial component (or a composition containing it) and placed in the user's eye for safe and comfortable wear.

Ophthalmically Acceptable: As used herein, the term "ophthalmically acceptable" refers to an contact lens care solution or component thereof that is compatible with ocular tissue, i.e., it does not cause significant or undue detrimental effects when brought into contact with ocular tissue.

Synergistically-effective: As used herein, the term "synergistically-effective" and "synergistically-antimicrobial" refer to any combined amount antimicrobial compound or compounds that exhibit synergistic biocidal, antimicrobial, antibacterial, or antifungal activity against at least one microbe. As used herein, "synergistic" and "synergistically" refer to the effect achieved with a combination of components when that effect is greater than the effect achieved with either component alone. As used herein, "synergistic" and "synergistically" includes additive effect.

Silver: as used herein, the term 'silver' refers to silver and its salts.

DETAILED DESCRIPTION OF THE INVENTION

Disclosed herein are ophthalmic cleaning systems and methods for their use, which comprise an ophthalmic solution and lens case, wherein the solution includes dual disinfectants and the lens case includes silver. When the lens case is combined with the solution according to the system of the present invention, it surprisingly exhibits antimicrobial activity which is above and beyond the antimicrobial activity of either the case alone or the solution alone. This unexpected synergistic activity may be seen at a time which may be best suited to provide a benefit to a non-compliant user. A non-compliant user is one who does not follow their doctor's or their solution manufacturer's instructions with regards to lens care.

The lens case may be impregnated with the silver, which may be released into the ophthalmic solution. By way of example, and not of limitation, the lens case may be molded from a plastic resin which includes antibacterial metal or metal ions.

Commercially-available silver-releasing contact lens cases have been tested for silver release. Each well of the lens cases were filled with 3 mL of Dulbecco's PBS (without calcium and magnesium, Invitrogen, Cat#141900) and then incubated at 25° C. The silver-releasing contact lens case Microblock™, also known as ProGuard™, from the CIBA Vision Corporation in Atlanta, Ga. has demonstrated measurable release of silver into Dulbecco's phosphate-buffered saline with a range of 16-45 μg/L over 28 days. More or less silver release than this range may also be employed, although generally amounts of released silver at this range or more are preferred. For example, amounts of silver release from 1 to 100, 250, 500 or even 1000 ug/L over 28 days using this method of measuring silver release may be employed.

In one embodiment, the present ophthalmic solutions comprise a liquid aqueous medium and at least dual disinfecting components comprising a combination of polyquaternium-1 and a biguanide, the combination being present in an amount effective to disinfect a contact lens contacted with the composition. The solution may further include other components which are typically found in multi-purpose solutions.

Such additional components may include: a surfactant component, preferably a nonionic surfactant, in an amount effective in cleaning a contact lens contacted with the composition; a buffer component in an amount effective in maintaining the pH of the composition within a physiologically acceptable range; an effective amount of a viscosity inducing component; and an effective amount of a tonicity component.

The present compositions may also include an effective amount of a chelating or sequestering component, more preferably in a range of less than 0.05% (w/v). Each of the components, in the concentration employed, included in the solutions and the formulated solutions of the present invention preferably are ophthalmically acceptable. In addition, each of the components, in the concentration employed, included in the present solutions is soluble in the liquid aqueous medium.

The present compositions are substantially ophthalmically optimized. An ophthalmically optimized composition is one which, within the constraints of component chemistry, minimizes ocular response, or conversely delivers ophthalmic benefit to the lens-wearing eye.

Additional antimicrobial components may be added to the present compositions. The presently useful additional antimicrobial components include chemicals which derive their antimicrobial activity through a chemical or physiochemical interaction with microbes or microorganisms, such as those contaminating a contact lens. Suitable antimicrobial components are those generally employed in ophthalmic applications and include, but are not limited to: quaternary ammonium salts used in ophthalmic applications such as benzalkonium halides, and biguanides, such as salts of alexidine, alexidine-free base, salts of chlorhexidine, hexamethylene biguanides, polyhexamethylene biguanides, and salts thereof, antimicrobial polypeptides, and the like and mixtures thereof.

The antimicrobial components useful in the present invention preferably are present in the liquid aqueous medium in concentrations in the range of from about 0.00001% or about 0.0001% or about 0.0005% to about 0.001 or about 0.01% (w/v). More preferably, the polyquaternium-1, biguanide and any additional antimicrobial components are present in the liquid aqueous medium at an ophthalmically acceptable or safe concentration such that the user can remove the disinfected lens from the liquid aqueous medium and thereafter directly place the lens in the eye for safe and comfortable wear, with minimal, if any, incidence of corneal epithelial punctate fluorescein staining.

The present invention incorporates the polyquaternary ammonium compound poly[(dimethyliminio)-2-butene-1,4-diyl chloride], α-[4-[tris(2-hydroxyethyl) ammonio]-2-butenyl]-ω-[tris(2-hydroxyethyl)ammonio]-dichloride, known as Polyquaternium-1 (Onyx Corporation, Jersey City, N.J.) in the range of from about 0.000075% or about 0.0005% or about 0.0001% to about 0.005 or about 0.01 wt %. A biguanide is also used as part of the disinfecting system of the present invention. Many biguanides may be suitable. Representative biguanides include polyhexamethylene biguanide (PHMB) and alexidine. It is also anticipated that the present invention would work with the biguanides disclosed in U.S. Pat. No. 6,936,640. The biguanide may be present in the range of from about 0.00001% or about 0.0005% to about 0.005% or about 0.01 wt %.

If a solution to clean lenses is to contact the eyes (either the composition itself or via a contact lens), it is preferred that the individual solution components are present at ophthalmically acceptable concentrations such that ocular irritation or user discomfort are minimized or eliminated. An ophthalmic composition may comprise several ingredients and the amounts of the ingredients relative to each other may impact the ophthalmic acceptability of the composition. A skilled artisan knows how to prepare an ophthalmically acceptable composition by varying the individual amounts of ingredients.

Compositions herein disclosed may also include a surfactant component, preferably a nonionic surfactant, in an amount effective to clean a contact lens contacted with the composition, a buffer component in an amount effective in maintaining the pH of the composition within a physiologically acceptable range (if the composition directly will contact the eyes), an effective amount of a viscosity inducing component, and/or an effective amount of a tonicity component. The present compositions also may include an effective amount of a chelating or sequestering component, more preferably in a range of less than about 0.05% (w/v). The compositions disclosed herein preferably are ophthalmically acceptable taking into account each of the components in the concentrations employed relative to each other. In addition, each of the components preferably is employed in amounts that permit complete solubility in the compositions.

If the disclosed compositions will directly contact the eyes, it is preferred that the compositions have a pH in the physiologically acceptable range of about 4, about 5, or about 6 to about 8, about 9, or about 10. In particular, the solution preferably has a pH in the range of about 6 to about 8. In order to achieve or maintain the desired pH, a buffer component in an amount effective to maintain the pH may be required. The buffer component may include one or more phosphate or tromethamine (TRIS, 2-amino-2-hydroxymethyl-1,3-propanediol) buffers, for example, combinations of monobasic phosphates, dibasic phosphates, and the like, or tromethamine and tromethamine hydrochloride. Particularly useful phosphate buffers are those selected from phosphate salts of alkali metals. Examples of suitable phosphate buffers include one or more of sodium phosphate dibasic ($Na_2HPO_4$), sodium phosphate monobasic ($NaH_2PO_4$), and the corresponding potassium phosphate salts. The buffer component also may include boric acid and/or sodium borate (e.g., sodium borate 10 hydrate). The buffer component also may include an amino acid such as taurine. Buffer components typically are used in amounts from about 0.01% or about 0.02% to about 0.5% (w/v) or about 2% (w/v).

The disclosed compositions may further comprise effective amounts of other components, such as a detergents or surfactants, viscosity-inducing or thickening components, chelants or sequesterants and tonicity agents. The additional component or components may be selected from any materials known to be useful in contact lens care compositions and may be included in amounts effective to provide the desired effect or benefit. If an additional component is included, it preferably is compatible with the other components of the composition under typical use and storage conditions. For example, the additional component or components preferably do not impact adversely the antimicrobials described herein.

A surfactant may be added to the disclosed compositions to aid in cleaning, e.g., to at least aid in removing debris or deposit material from a contact lens contacted with the solution. Some exemplary surfactant(s) include, but are not limited to, nonionic surfactants (e.g., polysorbates like polysorbate 20, (i.e. Tween® 20), 4-(1,1,3,3-tetramethylbutyl) phenol/poly(oxyethylene) polymers (e.g. Tyloxapol®), poly(oxyethylene)-poly(oxypropylene) block copolymers, and combinations of these and/or other surfactants.

Nonionic surfactants are preferred for some embodiments of compositions disclosed herein. Nonionic surfactants include poly(oxyethylene)-poly(oxypropylene) block copolymers (poloxamers), which may be obtained commercially from the BASF Corporation under the trademarks Pluronic® or Tetronic®. Pluronic® block copolymers generally can be described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol or glycerin. An ethylene oxide then may be added to sandwich the hydrophobe between hydrophile groups. Tetronic® surfactants are known as poloxamines and are symmetrical block copolymers of ethylene diamine with polyoxyethylene and polyoxypropylene.

In some embodiments, the block copolymers may have average molecular weights in the range of about 2500 to about 30,000 Daltons, more preferably about 6000 to about 18,000 Daltons. Exemplary block copolymer surfactants include: poloxamer 108, poloxamer 188, poloxamer 237, poloxamer 238, poloxamer 288 poloxamer 407, Pluronic P103, Tetronic® 904, Tetronic® 1107, Tetronic® 1304 (mol. wt. 10,500), and Tetronic® 1307.

The amount of surfactant component present, if any, varies over a wide range depending on a number of factors, including, the particular surfactant(s) used, any other components in the composition, and the like. Typically, the amount of surfactant may be at least about 0.005% or about 0.01% and at most about 0.1%, about 0.5%, or about 1.0% (w/v). In another embodiment, the surfactant concentration may be about 0.05% to about 0.20% (w/v).

The viscosity-inducing components employable in the present compositions preferably are those that are effective at low or reduced concentrations, are compatible with other components of the present compositions, and are nonionic. Such viscosity inducing components may act to enhance and/or prolong the cleaning and wetting activity of any surfactant component, condition the lens surface making it more hydrophilic/less lipophilic, and/or to act as a demulcent in the eye. Increasing solution viscosity also may provide a film on the lens to facilitate comfortable wear. The viscosity-inducing component also may act to cushion the impact of contact lens insertion on the surface eye and also may serve to alleviate eye irritation.

Suitable viscosity-inducing components include, but are not limited to, water soluble natural gums, cellulose-derived polymers and the like. Natural gums include guar gum, gum tragacanth, and the like. Cellulose-derived polymers include hydroxypropyl cellulose, hydroxypropylmethyl cellulose, methyl cellulose, hydroxyethyl cellulose, and the like. Preferred viscosity-inducing agents include cellulose derivatives (polymers), and mixtures thereof. A particularly useful viscosity inducing component is hydroxypropylmethyl cellulose (HPMC).

The viscosity-inducing component is used in an amount effective to increase the viscosity of the solution, preferably to a viscosity in the range of about 1.5 to about 30 cps, or even as high as about 75 cps (measured at 25° C.), preferably as determined by The United States Pharmacopeial Convention (USP) Test Method No. 911 (USP 23, 1995). To achieve this range of viscosity increase, about 0.01% to about 5% (w/v), or about 0.05% to about 0.5% (w/v), of a viscosity-inducing component typically is employed.

A chelating or sequestering component preferably is included in an amount that enhances the efficacy of the antimicrobial component and/or complexes with any metal ions to more effectively clean the contact lens.

A wide range of organic acids, amines or compounds which include an acid group and an amine function are capable of acing as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts (e.g., trisodium citrate), tartaric acid and its salts, and the like and mixtures thereof, are useful as chelating components.

Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution. In a very useful embodiment, particularly when the chelating component is EDTA, salts thereof and mixtures thereof, a reduced amount is employed, for example, in the range of less than about 0.05% (w/v) or even about 0.02% (w/v) or less. Such reduced amounts of chelating component have been found to be effective in the present compositions while, at the same time, providing for reduced discomfort and/or ocular irritation.

The liquid aqueous medium used in conjunction with the present compositions is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200-mOsmol/kg for example, about 300 or about 350, to about 400 mOsmol/kg. The liquid aqueous medium more preferably is substantially isotonic or hypotonic (for example, slightly hypotonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts and non-ionic polyols. Sodium chloride (NaCl) and/or potassium chloride (KCl) and the like are very useful tonicity components, as are propylene glycol, glycerin, sorbitol, mannitol and the like. The amount of tonicity component included is effective to provide the desired degree of tonicity to the solution. Such amount may be, for example, in the range of about 0.2% to about 1.5% (w/v). If a combination of sodium chloride and potassium chloride is employed, it is preferred that the weight ratio of sodium chloride to potassium chloride be in the range of about 3 to about 6 or about 8.

Methods for treating a contact lens using the antimicrobial component described herein are included within the scope of the invention. Such methods comprise contacting a contact lens with such a composition at conditions effective to provide the desired treatment to the contact lens. Contacting parameters in include, among others, temperature, pressure and time. Contacting temperature may be in the range of about 0° C. to about 100° C., more preferably in the range of about 10° C. to about 60° C., and still more preferably in the range of about 15° C. to about 30° C. Contacting at about ambient temperature is typical. The contacting may occur at about atmospheric pressure. The contacting preferably occurs for a time in the range of about 5 minutes or about 1 hour to about 2 hours, about 4 hours, about 6 hours, or about 12 hours or more. As described herein, such a composition may include other ingredients including, but not limited to, a viscosity enhancing agent to, for example, increase the residence time of the composition in the eye or to increase user comfort.

A contact lens can be contacted with a liquid aqueous medium in association with the method of the present invention by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens with the liquid aqueous medium prior to returning the lens to a wearer's eye. In one embodiment, the lens can be substantially free of the liquid aqueous medium prior to returning the lens to a wearer's eye. However, the method may also be as simple as removing the lens from the lens case, and placing the lens directly in an eye either with or without removing the liquid aqueous medium prior to placing the lens in the wearer's eye.

EXAMPLE 1

The specific test procedure for testing antimicrobial activity against specified test organisms is as follows: A 3-mL aliquot of test sample is transferred into a single well of either an Abbott Medical Optics Inc. contact lens case or a single well of a CIBA Pro-Guard® contact lens case. Sterile Dulbecco's Phosphate-Buffered Saline with 0.05 w/v % Polysorbate 80 (DPBST) is transferred into a separate single well of the same contact lens case and used as a control. All samples and control are stored at 20-25° C. throughout the duration of the test. Test cultures of specified test organisms are cultured and prepared in the conventional manner using Trypiticase Soy Agar (TSA) as the growth medium. The challenge organism inoculum is adjusted to approximately $1 \times 10e7$-$1 \times 10e8$ CFU/mL in DPBST. Ten μL of culture inoculum is added to 3.0 mL of each test sample and control, so that the final inoculum level is in the range of $1 \times 10e5$ to $1 \times 10e6$ CFU (colony forming units) per mL of specified test organism. Contact time intervals for testing activity against the specified test organism are typically within 4 or 6 hours, e.g., 15 min, 30 min, 45 min, 1 hour, 2 hours, 4 hours and 6 hours, to remain within the intended product label instructions for maximum contact lens soak time.

Following incubation, the number of surviving organisms was enumerated by serial dilution and culture on TSA medium. An appropriate neutralizing disinfectant medium was used in the initial dilution (e.g. Dey Engly Neutralizing Broth media).

Following incubation, the numbers of colony-forming-units (CFU) were counted and the $Log_{10}$) reduction in viable number calculated based on the initial time zero challenge inoculum in the test solution.

The example ophthalmic solution 1 is prepared with the components and amounts listed in Table 1. The components are added to purified water at room temperature (e.g., about 25° C.) with gentle stirring in the order: Tetronic 904, NaCl, buffers, EDTA and then the disinfecting agents.

TABLE 1

| Ingredients | Solution 1 wt (%) |
|---|---|
| Alexidine, ppm | 0.00016 |
| PQ-1, ppm | 0.0003 |
| EDTA | 0.05 |
| NaCl | 0.25 |
| Boric acid | 0.60 |
| Sodium borate decahydrate | 0.15 |
| Sodium citrate dihydrate | 0.65 |
| Tetronic 904 | 0.10 |

As shown in Table 2, when ophthalmic solution 1 is utilized within a lens case which elutes silver, a synergistic disinfecting effect may be seen. In fact, the synergistic effect is seen at all time points tested in the first hour. By way of example, ophthalmic solution 1 in the non-silver case demonstrated a 2.4 log kill after 45 min; however when ophthalmic solution 1 was utilized in the silver case it demonstrated a 4.0 log kill. This 4.0 log kill is significantly larger than the individual total log kill, which is only 2.5 (2.4 from ophthalmic solution 1 and 0.1 from the silver lens case).

These results show that the PQ-1/biguanide solution reached its maximum disinfecting capability significantly faster when utilized in conjunction with a silver lens case due to their synergistic disinfecting capability. Such speed of disinfection could provide a useful benefit to a non-compliant user.

TABLE 2

*Stenotrophomonas maltophilia* ATCC 15099
$Log_{10}$ kill

|  | Solution 1 | | DPBST | |
| --- | --- | --- | --- | --- |
| Time | Ciba Proguard case | AMO case | Ciba Proguard case | AMO case |
| 15 min | 1.3 | 1 | 0.1 | 0.2 |
| 30 min | 2.4 | 1.8 | 0.1 | 0.1 |
| 45 min | 4 | 2.4 | 0.1 | 0.1 |
| 1 h | 5.1 | 4.2 | 0.1 | 0.1 |
| 2 h | 5.1 | 5.1 | 0.1 | 0.1 |
| 4 h | 5.1 | 5.1 | 0.1 | 0.1 |

EXAMPLE 2

In this experiment, the components shown in Table 3 were mixed as described above. These solutions demonstrate a real-world example where the biguanide may be taken-up (bound) by a contact lens over time, leading to solution depletion of that component.

TABLE 3

| Ingredients | DT1006-66-1 | DT1006-66-2 | DT1006-66-3 |
| --- | --- | --- | --- |
| Alexidine (ppm) | 0.20 | 0.40 | 0.60 |
| PQ-1 (ppm) | 3.00 | 3.00 | 3.00 |
| EDTA | 0.05 | 0.05 | 0.05 |
| NaCl | 0.25 | 0.25 | 0.25 |
| Boric Acid | 0.6 | 0.6 | 0.6 |
| Sodium borate 10H20 | 0.15 | 0.15 | 0.15 |
| Sodium citrate 2H20 | 0.65 | 0.65 | 0.65 |
| Tetronic 904 | 0.10 | 0.10 | 0.10 |

As shown in Table 4, all of the solutions demonstrate synergistic antimicrobial activity against *S. maltophilia*, with the most prominent demonstration starting at approximately 2 hours. That is, this data again shows that the PQ-1/biguanide solution reached its maximum disinfecting capability significantly faster when utilized in conjunction with a silver lens case due to their synergistic disinfecting capability. Such speed of disinfection could provide a useful benefit to a non-compliant user.

TABLE 4

Organisms
*Stenotrophomonas maltophilia* ATCC 15099
Log10 kill

| Time | DT1006-66-1 | DT1006-66-2 | DT1006-66-3 | DPBST |
| --- | --- | --- | --- | --- |
| Pro-Guard CIBA case | | | | |
| 15 min | 0.3 | 0.4 | 0.4 | 0.1 |
| 30 min | 0.4 | 0.7 | 0.9 | 0.2 |
| 45 min | 0.7 | 1.2 | 1.6 | 0.2 |
| 1 h | 1 | 1.5 | 2 | 0.2 |
| 2 h | 1.8 | _2.9_ | _4.9_ | 0.2 |
| 4 h | _3.5_ | _4.9_ | 4.9 | 0.2 |
| 6 h | _4.9_ | _4.9_ | 4.9 | 0 |
| AMO case | | | | |
| 15 min | 0.3 | 0.4 | 0.4 | 0.2 |
| 30 min | 0.5 | 0.6 | 0.9 | 0.2 |
| 45 min | 0.7 | 1.1 | 1.4 | 0.2 |
| 1 h | 1.1 | 1.4 | 1.8 | 0.2 |
| 2 h | 1.4 | 2.1 | 2.8 | 0.1 |
| 4 h | 2.2 | 3.3 | 4.9 | 0.2 |
| 6 h | 2.9 | 4.3 | 4.9 | 0 |

EXAMPLE 3

In this Example, the solutions shown in Table 3 were tested to determine their activity against *Delftia acidovorans*. As shown in Table 5, the silver lens case with the PQ-1/biguanide solution provided synergistic antimicrobial activity against this microorganism. That is, this data again shows that the PQ-1/biguanide solution reached its maximum disinfecting capability significantly faster when utilized in conjunction with a silver lens case due to their synergistic disinfecting capability. Such speed of disinfection could provide a useful benefit to a non-compliant user.

TABLE 5

Organisms
*Delftia acidovorans* ATCC 17438
Log10 kill

| Time | DT1006-66-1 | DT1006-66-2 | DT1006-66-3 | DPBST |
| --- | --- | --- | --- | --- |
| Pro-Guard CIBA case | | | | |
| 15 min | 0.1 | 1.4 | 2.6 | 0.2 |
| 30 min | 2.4 | 3.6 | 4.5 | 0.1 |
| 45 min | 4.2 | 4.5 | 4.5 | 0.1 |
| 1 h | 4.5 | 4.5 | 4.5 | 0.1 |
| 2 h | 4.5 | 4.5 | 4.5 | 0.1 |
| 4 h | 4.5 | 4.5 | 4.5 | 0.1 |
| 6 h | 4.5 | 4.5 | 4.5 | 0.2 |
| AMO case | | | | |
| 15 min | 0.3 | 2.1 | 2.2 | 0.2 |
| 30 min | 1.7 | 2.2 | 2.3 | 0.1 |
| 45 min | 3.2 | 3.1 | 3.7 | 0.2 |
| 1 h | 4 | 3.6 | 4.5 | 0.1 |
| 2 h | 4.5 | 4.5 | 4.5 | 0.1 |
| 4 h | 4.5 | 4.5 | 4.5 | 0.1 |
| 6 h | 4.5 | 4.5 | 4.5 | 0 |

As shown in Table 5, all of the solutions demonstrate synergistic antimicrobial activity against *D. acidovorans*, with even the most depleted solution showing the activity at 1 hour That is, this data again shows that the PQ-1/biguanide solution reached its maximum disinfecting capability significantly faster when utilized in conjunction with a silver lens case due to their synergistic disinfecting capability. Such speed of disinfection could provide a useful benefit to a non-compliant user.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of disinfecting a contact lens comprising contacting a contact lens with a solution in a silver-releasing contact lens case, wherein the solution comprises:
   0.00016 wt % alexidine:
   0.0003 wt % polyquaternium-1;
   0.05 wt % ethylenediaminetetraacetic acid;
   0.25 wt % sodium chloride;
   0.60 wt % boric acid;
   0.15 wt % sodium borate decahydrate;
   0.65 wt % sodium citrate dihydrate; and
   0.10 wt % of a poly(oxyethylene)-poly(oxypropylene) block copolymer and further wherein the method provides synergistic antimicrobial activity against at least one gram-negative bacterium.

2. The method of claim 1 wherein the lens case releases from about 1 ug/L to about 1000 ug/L of silver ions into the solution.

* * * * *